(12) United States Patent
Neitsch

(10) Patent No.: US 7,847,934 B2
(45) Date of Patent: Dec. 7, 2010

(54) METHOD FOR CORRECTING SPECTRAL INTERFERENCE IN ICP EMISSION SPECTROSCOPY (OES)

(75) Inventor: Lutz Neitsch, Hamminkeln (DE)

(73) Assignee: Spectro Analytical Instruments GmbH, Kleve (DE)

( * ) Notice: Subject to any disclaimer, the term of this patent is extended or adjusted under 35 U.S.C. 154(b) by 297 days.

(21) Appl. No.: 12/159,887

(22) PCT Filed: Nov. 27, 2006

(86) PCT No.: PCT/EP2006/011329
§ 371 (c)(1),
(2), (4) Date: Jul. 2, 2008

(87) PCT Pub. No.: WO2007/076907

PCT Pub. Date: Jul. 12, 2007

(65) Prior Publication Data
US 2009/0014635 A1    Jan. 15, 2009

(30) Foreign Application Priority Data
Jan. 3, 2006   (DE) .................. 10 2006 000 805

(51) Int. Cl.
*G01J 3/30* (2006.01)
(52) U.S. Cl. .................................... 356/316
(58) Field of Classification Search ............. 356/316
See application file for complete search history.

(56) References Cited

U.S. PATENT DOCUMENTS
5,742,525 A * 4/1998 Ye .................... 702/81
6,418,383 B1   7/2002 Wang

FOREIGN PATENT DOCUMENTS
EP        0415151        3/1991

(Continued)

OTHER PUBLICATIONS

E.H. Van Veen, "Application of mathematical procecures to background correction and multivariate analysis in inductively coupled plasma-optical emission spectrometry", Spectrochimica Acta, Part B, vol. 53, p. 639-669, 1998.

(Continued)

*Primary Examiner*—Tarifur Chowdhury
*Assistant Examiner*—Abdullahi Nur
(74) *Attorney, Agent, or Firm*—Connolly Bove Lodge & Hutz LLP

(57) ABSTRACT

The present invention relates to a method for correcting spectral interference in a spectrum which is determined using an inductively coupled plasma spectrometer (ICP) for analysing element contents of a liquid or gaseous sample, comprising the following steps:
recording the spectrum of a matrix solution containing all spectrally interfering components, which are also contained in the sample, in a first concentration;
recording the spectrum of the matrix solution in at least one dilution of the first concentration;
regressing the signal intensities obtained in steps a. and b. against the concentration for a number of wavelength positions;
calibrating the spectrometer, background correction using the values determined from the regression in step c. and determining the calibration function $c=f(I)$;
recording the sample spectrum using at least one analyte which is contained therein;
determining the concentration of the spectrally interfering components in the sample using the results obtained in step c. for wavelength positions at which no line of the analyte of the sample is present; and
determining the sample signal which is characteristic of the analyte concentration by forming the difference between the spectrum from step e. and the calculated matrix spectrum in a dilution which was calculated in step f., wherein the calibration function $c=f(I)$ is used.

10 Claims, 4 Drawing Sheets

FOREIGN PATENT DOCUMENTS

Figure 1:
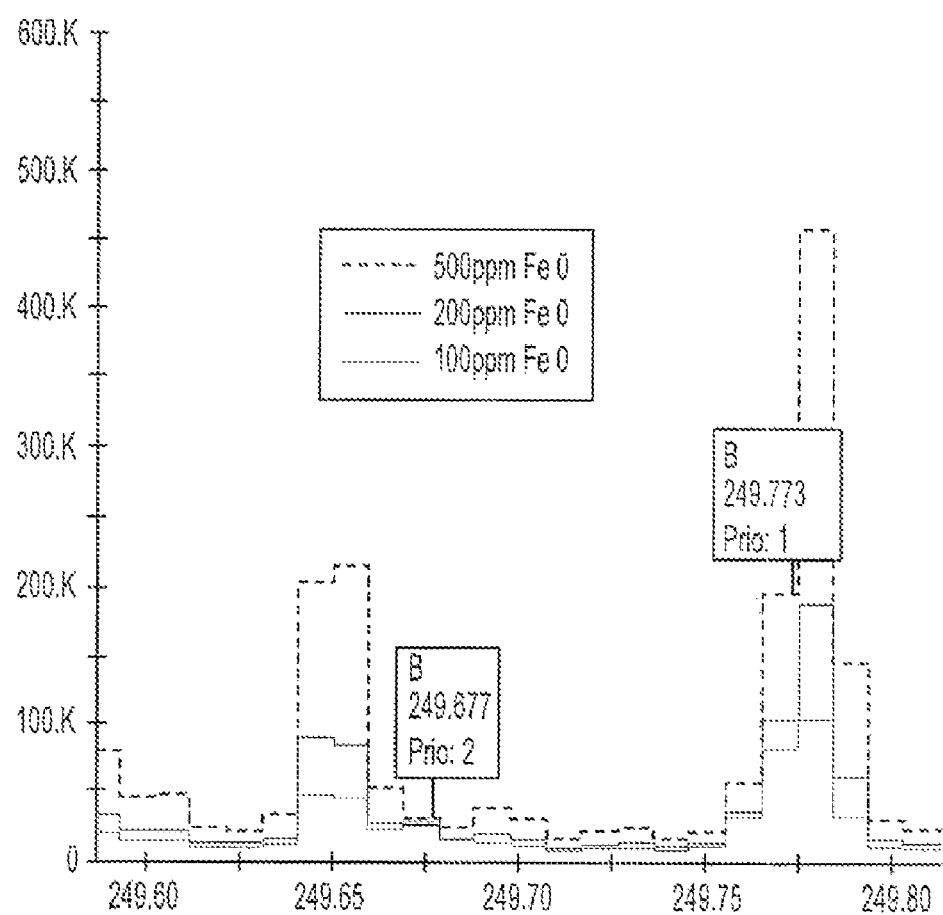

| | | |
|---|---|---|
| EP | 1004005 | 5/2000 |
| GB | 2291184 | 1/1996 |

OTHER PUBLICATIONS

M. Griffiths et al., "Comparison of traditional and multivariate calibration techniques applied to complex matrices using inductively coupled plasma atomic emission spectroscopy", Journal of Analytical Atomic Spectrometry, vol. 15, p. 967-972, 2000.

E.H. Vanveen et al., On the use of line intensity ratios and power adjustments to control matrix effects in inductively coupled plasma optical emission spectrometry, Journal of Analytical Atomic Spectrometry, vol. 14, p. 8131-838, 1999.

* cited by examiner

METHOD FOR CORRECTING SPECTRAL INTERFERENCE IN ICP EMISSION SPECTROSCOPY (OES)

CROSS-REFERENCE TO RELATED APPLICATIONS

This application is a 35 U.S.C. §371 Application of International Application No. PCT/EP2006/011329, filed Nov. 27, 2006, claiming the benefit of German Application No. 10 2006 000 805.7, filed Jan. 3, 2006, the entire disclosures of which are incorporated herein by reference in their entireties.

The present invention relates to a method for correcting spectral interference in ICP emission spectroscopy with the features of the preamble of claim 1.

TECHNICAL BACKGROUND

Description of ICP OES and the Typical Areas of Use

Because of the versatility of the method and also because of the speed of the analysis, ICP emission spectroscopy is one of the most important techniques of instrumental elemental analysis in which a plurality of elements can be quantitatively determined simultaneously. Spectrometers of this type are used for process monitoring, quality control and environmental analysis and bear the basic load of routine analysis in analysis laboratories.

The principle of ICP emission spectroscopy is, for example, described in Montaser (A. Montaser, D. W. Golightly: Inductively Coupled Plasmas in Analytical Atomic Spectroscopy, John Wiley & Sons, New York, 1992).

The generally liquid samples are atomised into an aerosol and introduced into an inductively coupled plasma, wherein Ar is used as the plasma gas because of its easy ionisability. Molecules of the sample are divided into their atomic components, partially ionised and electronically excited by the high thermal energy with temperatures of up to 10,000 K.

Owing to the falling back of electrons of excited atoms and ions into energetically lower electron configurations, an intensive emission spectrum is obtained which is composed of radiation of element-specific wavelengths of the elements contained in the sample as well as element-non-specific background radiation. The element-specific radiation consists of a plurality of so-called spectral lines. The background radiation is structured molecular spectra as well as a continuum which spans the entire wavelength range used in ICP OES. The continuum radiation is produced by the recombination of argon ions with electrons and by the bremsstrahlung of the electrons. A further potential component is scattered light, which is produced by the reflection of intensive lines on components of the spectrometer.

Description of the Traditional Evaluation of Emission Spectra

As ICP OES is an indirect method, a calibration with samples (standard) with known contents has to be carried out for the quantitative determination of contents of the elements.

Different evaluation models exist. Information which is contained in the measured emission spectra is always used here to determine the contents.

Despite mathematically more complex data reduction techniques (for example Kalman filter, MLR, PLS, PCR, and further methods, see, for example, E. H. Van Veen, M. T. C., de Loos-Vollebregt, Spectrochim. Acta Part B 53 (1998), 639-669), the traditional, conventional evaluation generally continues to be used, not least because of the simpler reproducibility and the less complex calibration work in comparison to the multi-variant methods.

In traditional evaluation, the radiation intensity at the wavelength of a suitable emission line of the elements to be analysed is determined. For calibration, the known contents of the elements of the standard samples are regressed against the measured intensity of an emission line by means of a polynomial.

The concentration of the element in an unknown sample is determined by applying the corresponding calibration function.

Description of Typical Interference (Spectral and Non-Spectral)

Signals of the spectral lines can be disturbed by spectral and non-spectral effects. The interference last mentioned influences the intensity of the element-specific radiation fraction. This interference is produced by components of the sample which have an influence on the sample input, the atomisation or the conditions in the plasma.

Spectral interferences are additive contributions to the signal of the element-specific spectral lines, caused by unstructured background radiation or overlapping spectral lines of another element or a molecule. The interferences last mentioned depend on the presence of the interfering sample component. However, the intensity of the unstructured background radiation may also depend on certain elements of the sample. In the simplest case, this is possible through scattered light of intensive lines.

Description of the Current Correction Methods

To take into account the background signal, the corresponding background signal may be determined separately by measuring an empty sample without analytes and deducted from the signal of the analyte sample. However, this method does not take into account any variations of the background level which can be produced, for example, by the presence of additional components in the sample.

A further method requires the definition of suitable background positions in the surroundings of the relevant analyte line. By measuring the signal at the defined background positions and determining a polynomial using the background signals, the background signal at the measuring position of the spectral analyte line can be interpolated and deducted from the analyte signal. The background positions are defined manually. In this case, spectra of typical samples or calibration samples are generally used to ensure that no unforeseen spectral structures are present at the background positions.

There are also methods for automatically finding positions of backgrounds. In the simplest case, flat regions with low intensities are recognised, which lie next to analytical lines (M. L. Salit, J. B. Collins, D. A. Yates, Appl. Spectrosc. 48 (1994), 915-925). The application of digital filters may also be used. The second derivation of the spectrum (G. Bauer, I. Rehana, W. Wegscheider, Spectrochim Acta Part B 43 (1988) 971-982) or a square wave development (P. Taylor, P. Schutyser, Spectrochim Acta Part B 41 (1986), 81-103) can be used here as the filter.

The background interpolation methods (manual or automatic) only operate to a limited extent to correct overlapping lines if the lines are located spectrally close to one another because, in these cases, interference and the analyte signal can no longer be clearly separated.

Line overlaps can be taken into account by interelemental correction (IEG). In this method, the concentrations for the calibration samples of analyte and interferers have to be known as a prerequisite. Moreover, these concentrations must not correlate. The interfering influence on the measurement signal is then taken into account in the regression. A corresponding amount more of calibration samples are to be measured as the interelemental interference, depending on the number of interferers, introduces additional degrees of freedom into the regression.

Complex analyte spectra are modelled from individual component spectra in multi-component analysis (MCA). To apply this technique, however, the samples of all individual components have to be measured separately (J. C. Ivaldi, D. Tracy, T. W. Barnard, W. Slavin, Spectrochim. Acta Part B, 47 (1992), 1361-1371).

The application of Kalman filters also requires individual component spectra and leads to comparable results (E. H. van Veen, S. Bosch, M. T. C. de Loos-Vollebregt, Spectrochim. Acta Part B, 49 (1994), 829-846).

The use of so-called "soft" modellings (PCR, PLS) requires a large number of calibration measurements, the composition of the calibration samples determining the applicability of the calibration to analyte samples (M. L. Griffiths, D. Svozil, P. J. Worsfold, S. Denham, E. H. Evans, J. Anal. At. Spectrom. 15 (2000), 967-972).

A method for the analysis of ICP emission spectra is known from the document U.S. Pat. No. 5,308,982, in which previously measured individual component spectra are used in order to be able to model a sample spectrum as a total of individual component spectra. The wavelength drift is compensated by evaluating derivations of the measured spectrum.

Finally, a method for background correction is known from the document EP 1004005 B1 in which Gaussian curves are adapted to the line of calibration spectra. The calibration spectra are then adapted to the spectra measured later until a minimum deviation is produced. The element concentration of the analytes can then be calculated from the fraction of the adapted curves suited to this element. A wavelength drift is monitored by monitoring argon lines. This method as a whole is complex.

Object

Proceeding from these known methods, the object of the present invention is to provide a method for correcting spectral interference in ICP emission spectroscopy, which allows an evaluation of spectra taking into account the spectral interference with a low outlay in the calibration.

This object is achieved by a method with the features of claim 1.

Because the recording of the spectrum of a matrix solution containing all the spectrally interfering components also contained in the sample firstly takes place in a first concentration, then the recording of the spectrum of this matrix solution is carried out in at least one dilution of the first concentration and by regression of the signal intensities obtained in these steps against the concentration for a number of wavelength positions, regression coefficients are obtained for the wavelength positions, the background spectrum with the spectral interference can be calculated for virtually any dilution.

If the calibration of the spectrometer and subsequently the recording of the sample spectrum takes place with at least one analyte contained therein, the signal of the analyte is obtained together with the matrix signal in an unknown dilution stage or concentration.

The determination of the concentration of the spectrally interfering components in the sample from the regression of signal intensities against the concentration, then takes place for wavelength positions in which no line of the analyte of the sample is present.

Finally, the determination of the characteristic sample signal for the analyte concentration follows by forming the difference of the spectrum from the measurement of the sample and the calculated matrix spectrum in a dilution which was calculated from the regression.

In this manner, a background is deducted from the signal of the sample spectrum, which takes into account the non-spectral and the spectral interference, specifically such that a virtually optimal result is produced with a low additional outlay. The additional outlay is limited to the measurement of two dilutions before the beginning of the calibration.

A particularly effective method is produced if the wavelength positions are identical with individual pixels of a CCD sensor.

DESCRIPTION OF THE NEW METHOD

Figure 2:
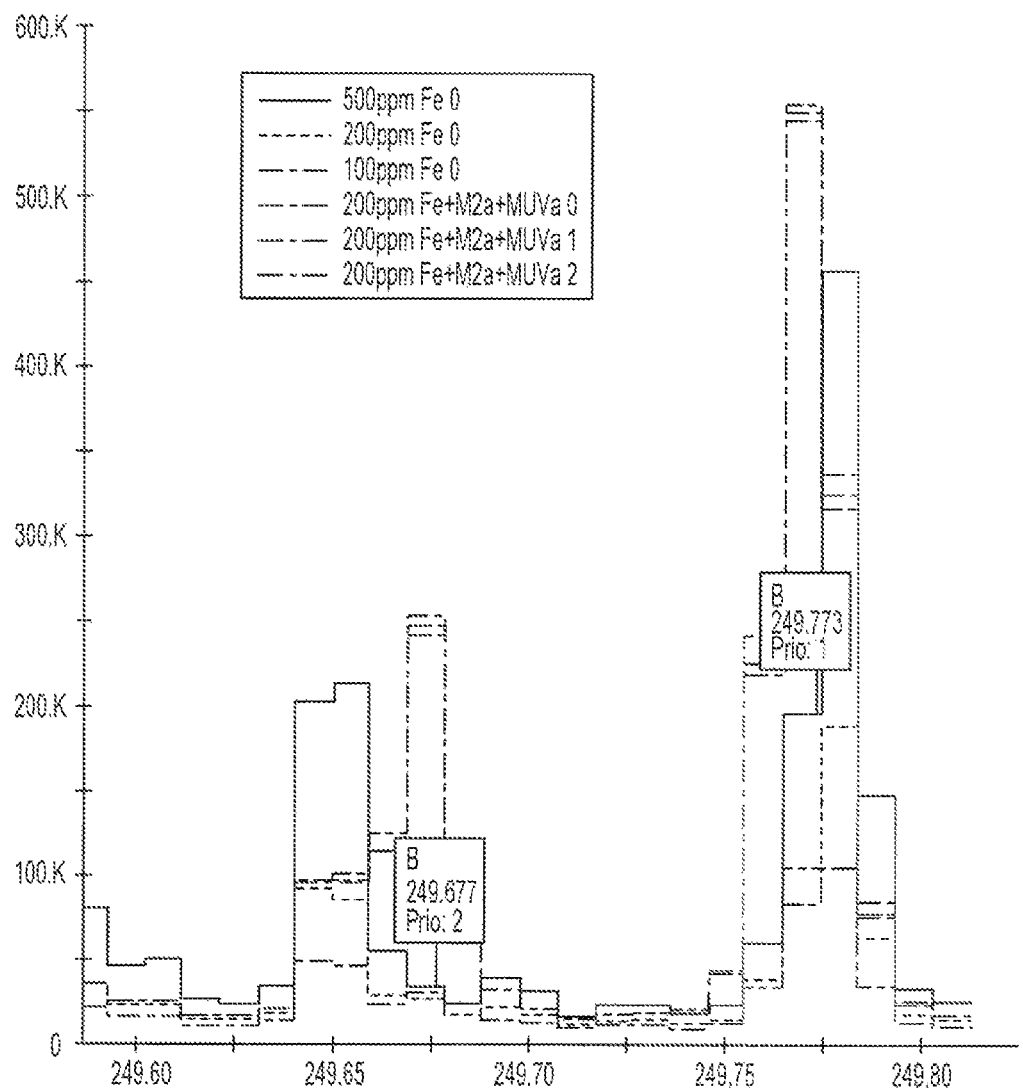
Figure 3:
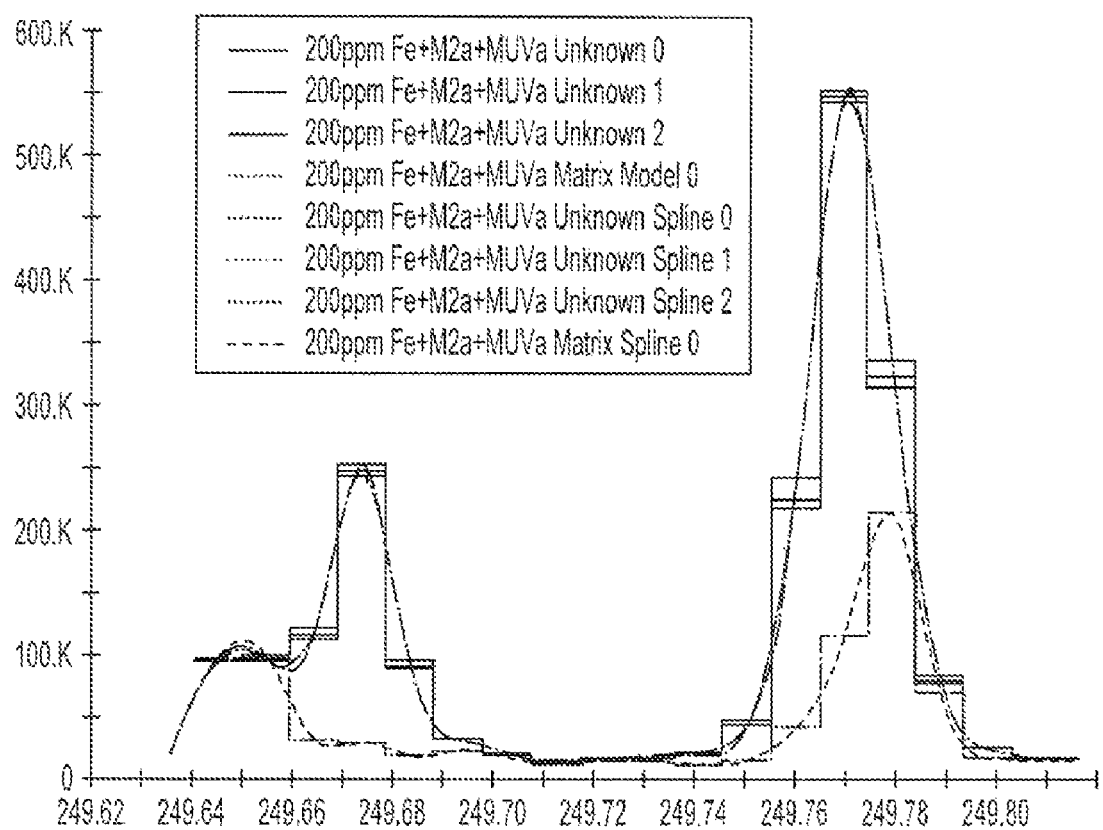
Figure 4:
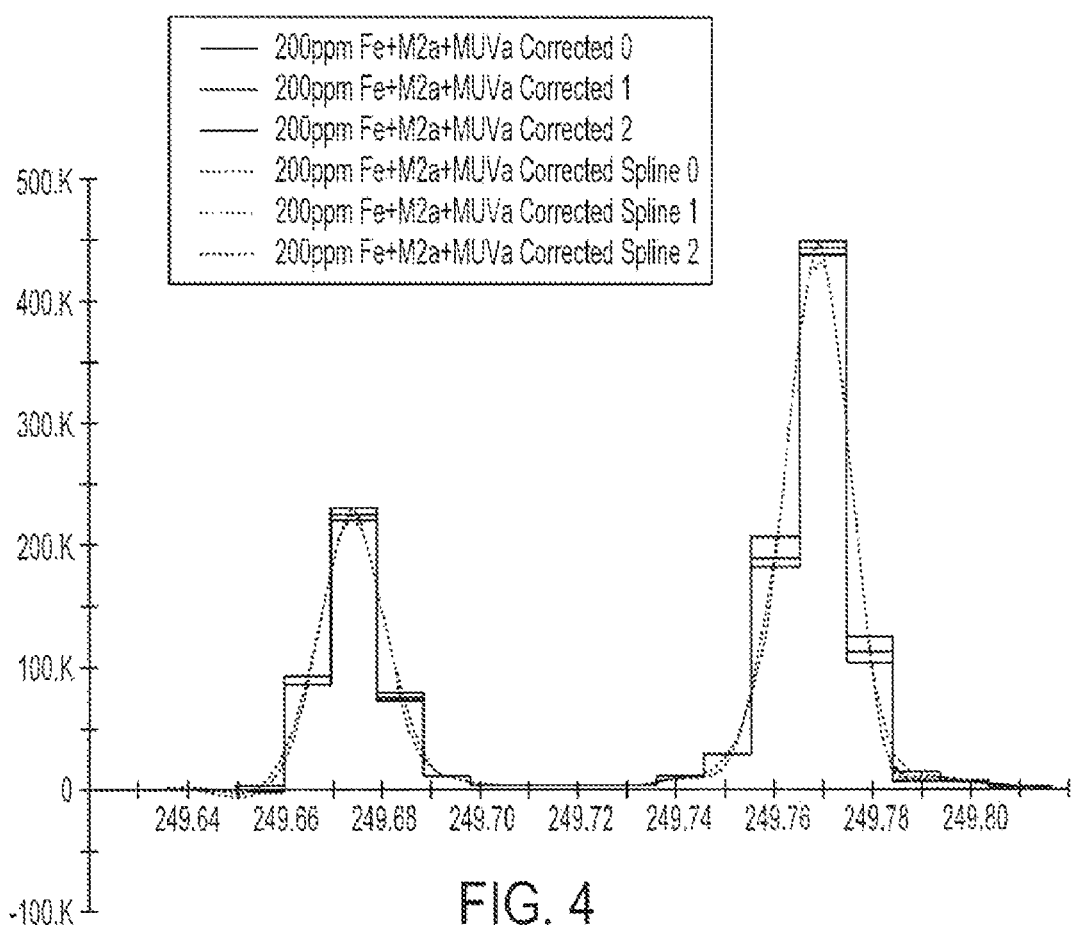

An embodiment of the method according to the invention will be described below with the aid of the figures, in which:

FIG. 1: shows a spectral range of 249.6 nm-249.8 nm of three samples with different iron contents;

FIG. 2: shows two boron lines at 249.677 nm and 249.773 nm;

FIG. 3: shows spectra of three repetition measurements of a sample, which contains 2 ppm boron and 200 ppm iron, together with a spectrum of the modelled matrix solution; and FIG. 4: shows background-corrected spectra of the individual measurements from FIG. 3 with added compensation functions.

FIG. 1 shows a small spectra range (249.6 nm-249.8 nm) of three samples with different iron contents (500 ppm, 200 ppm, 100 ppm).

As iron is very line-rich, particular for this element there are many overlaps with lines of other elements. However, the non-structured background also depends on the iron concentration, so the subtraction of a spectrum of an iron-containing sample leads to imprecisions. The markings give the position of two important boron lines. With the simultaneous presence of boron and iron, the boron lines were disturbed at 249.677 nm and 249.773 nm by the iron lines, as shown in FIG. 2.

Before the actual calibration, an additional solution (matrix solution) is added and measured in one or more dilutions. This matrix solution contains all the components which can contribute to a background variation (structured or non-structured). Apart from atomic components, solvents may also be added, the structured molecular bands of which (OH, CH) may overlap with spectral analyte lines.

In the example shown, iron is the interfering element. The three spectra with 500, 200 and 100 ppm are used as dilutions of the matrix solution and provide the dilution stage of the background. The number sequence 1.0, 0.4 and 0.2 may be selected as the relative measure for the dilution, in this case, for the three samples, the number 1.0 corresponding to the undiluted sample with 500 ppm iron. A relative measure is sufficient for the evaluation method for later modelling of the background spectrum, i.e. the absolute concentrations of the interferers are not insignificant.

In a selected spectral range (249.6 nm-249.8 nm) a regression of the signal intensities is then carried out against the relative dilution measure (dilution stage) for each wavelength position within the range.

$$I_{i,j} = a_{0,i} + a_{1,i} * C_{dilut,j}.$$

In this case, $C_{dilut,j}$ is the respective dilution stage of sample j. $I_{i,j}$ is the intensity of sample j at the position i and $a_{0,i}$ and $a_{1,i}$ are polynomial coefficients for position i. An adaptation to a polynomial of the first order is generally sufficient.

When using a plurality of dilution stages, in principle polynomials of higher orders may also be adapted to describe non-linear effects. Polynomial coefficients for each wavelength position observed are present as a result. By selecting the dilution stage, a background spectrum for subsequent measurements can now be modelled and thus a background correction carried out. A subsequent measurement may be a measurement of a calibration standard or that of an unknown sample. The method for this is described below:

1. Correlation analysis to determine suitable background positions: For each wavelength position the correlation of the analyte concentration and the intensities in the previously measured dilution samples of the matrix solution and the sample just observed, which contains the analytes, is determined. The analyte concentration in the dilution samples is zero, as these samples, by definition, may not have any spectral lines in the wavelength range observed. The sample just observed receives any concentration value which differs from zero, for example one. The absolute value is insignificant. All ranges are marked as suitable background positions for which correlations close to the value zero are obtained.
2. Determination of the background position, which can be used to determine the dilution stage: In this step, all the background positions which have a high sensitivity relative to the dilution stage are marked.
3. Determination of the dilution stage from the spectrum of the measurement just observed: For all the positions from Step 2, the dilation stage is determined here using the corresponding intensities and the polynomial coefficients:

$$C_{dilut,i}=(I_i-a_{0,i})/a_{1,i}.$$

In this case, $C_{dilut,i}$ is the dilution stage at the wavelength position i, $I_i$ is the intensity at the position i and $a_{0,i}$ and $a_{1,i}$ are the polynomial coefficients from the regression of the dilution solutions. The mean value $C_{dilut}$ is formed from the determined dilution stages.

4. Optimisation of the dilution stage: The dilution stage is varied until the mean value of the intensity differences of the sample spectrum and the modelled matrix spectrum at all background positions disappears except for a small difference.

As a variant of this 4-stage method, the dilution stage can also be increased iteratively from zero, until an intensity of the modelled matrix spectrum in the wavelength range of interest is higher than in the measured spectrum at the same position.

Using the dilution stage determined, from the measured sample spectrum and the polynomial coefficients, a matrix spectrum can be modelled, which is subtracted from the raw spectrum in order to obtain a background-corrected spectrum:

$$I_{corr,i}=I_{raw,i}-(a_{0,i}+a_{1,i}*C_{dilut}).$$

In the calibration step, the corrected intensities are used to determine the calibration equation.

In the analysis step in the measurement of samples of unknown contents, the corrected intensities are used by applying the calibration equation to find the content.

FIG. 3 shows the spectra of the three repetition measurements of the sample, which contains 2 ppm boron and 200 ppm iron together with a spectrum of the modelled matrix solution, which in this case is a modelling of the iron spectrum. For better visual display, compensation functions are added.

The background-corrected spectra of the three individual measurements are shown in FIG. 4. Compensation functions have also been added here for better visual display.

In summary, it can be stated that in ICP emission spectrometry for the analysis of elements of liquid and gaseous samples, the determination of the contents of samples of unknown composition is based on a calibration which is carried out with the aid of the measurement of calibration standards of known composition. All the evaluation methods are based on investigating the emission spectra, which contain element-specific emissions at specific wavelength positions. These signals are overlaid by spectral interference, which is produced from an unstructured background, structured background from molecule bands and structured lines of emissions of other analytical elements.

The present invention allows a spectral interference to be eliminated by the calibration of one or more dilutions of a matrix sample. In this case, the dilution stages are regressed against the intensities of the dilution spectra. For background correction, a background spectrum is modelled from a sample spectrum, the dilution stage of the background being determined. The background correction takes place by means of subtraction of the modelled spectrum from the raw spectrum.

Using the present invention, spectral backgrounds can therefore be taken into account without manual definition of backgrounds. Line overlaps of poorly dissolved spectra can be separated. In contrast to the subtraction of a measured background spectrum, sample-dependent variations of the background contribution are taken into account. In comparison to multi-component analysis, not all individual element standards are required. Only two standards more are required to describe the background. The complex combination of the element concentrations in the standard samples, as is necessary in the PLS or PCR methods, is dispensed with.

The invention claimed is:

1. A method for correcting spectral interference in a spectrum which is determined using an inductively coupled plasma spectrometer (ICP) for analyzing element contents of a liquid or gaseous sample, comprising the following steps:
    a. recording the spectrum of a matrix solution containing all spectrally interfering components, which are also contained in the sample, in a first concentration;
    b. recording the spectrum of the matrix solution in at least one dilution of the first concentration;
    c. regressing the signal intensities obtained in steps a. and b. against the concentration for a number of wavelength positions;
    d. calibrating the spectrometer, background correction using the values determined from the regression in step c. and determining the calibration function c=f(I);
    e. recording the sample spectrum using at least one analyte which is contained therein;
    f. determining the concentration of the spectrally interfering components in the sample using the results obtained in step c. for wavelength positions at which no line of the analyte of the sample is present; and
    g. determining the sample signal which is characteristic of the analyte concentration by forming the difference between the spectrum from step e. and the calculated matrix spectrum in a dilution which was calculated in step f., wherein the calibration function c=f(I) is used.

2. The method according to claim 1, wherein a regression of the intensities at predetermined wavelength positions against the dilution stage of the matrix solutions is carried out in a wavelength range of interest.

3. The method according to claim 2, wherein the background positions of a spectrum of a sample are determined using a correlation analysis of the intensities against the analyte content of an analytical element of interest.

4. The method according to claim 3, wherein the dilution stage of the spectrum of the sample is determined by means of the regression coefficients and the background intensities.

5. The method according to claim 2, wherein the dilution stage is determined by the iterative approximation of a modeled matrix spectrum to the measured spectrum.

6. The method according to claim 1, wherein the wavelength positions are identical to individual pixels of a CCD sensor.

7. The method according to claim 2, wherein the wavelength positions are identical to individual pixels of a CCD sensor.

8. The method according to claim 3, wherein the wavelength positions are identical to individual pixels of a CCD sensor.

9. The method according to claim 4, wherein the wavelength positions are identical to individual pixels of a CCD sensor.

10. The method according to claim 5, wherein the wavelength positions are identical to individual pixels of a CCD sensor.

* * * * *